(12) United States Patent
Kumar et al.

(10) Patent No.: US 8,911,363 B2
(45) Date of Patent: Dec. 16, 2014

(54) EFFICIENT CONTINUOUS FLOW IRRIGATION SYSTEM

(76) Inventors: Alka Kumar, Jaipur (IN); Atul Kumar, Jaipur (IN)

(*) Notice: Subject to any disclaimer, the term of this patent is extended or adjusted under 35 U.S.C. 154(b) by 281 days.

(21) Appl. No.: 13/540,849

(22) Filed: Jul. 3, 2012

(65) Prior Publication Data

US 2012/0271110 A1    Oct. 25, 2012

Related U.S. Application Data

(62) Division of application No. 11/871,051, filed on Oct. 11, 2007, now Pat. No. 8,226,549.

(30) Foreign Application Priority Data

Oct. 11, 2006    (IN) ............................ 2235/DEL/2006

(51) Int. Cl.
*A61B 1/12* (2006.01)
*A61B 1/00* (2006.01)
*A61M 1/00* (2006.01)
*A61B 1/015* (2006.01)
*A61M 3/02* (2006.01)

(52) U.S. Cl.
CPC ............. *A61B 1/015* (2013.01); *A61B 1/00071* (2013.01); *A61M 1/0058* (2013.01); *A61B 1/00068* (2013.01); *A61M 3/0258* (2013.01)
USPC ........... 600/156; 600/105; 600/121; 600/153; 600/155; 600/158

(58) Field of Classification Search
USPC ......... 600/105–107, 121–125, 153, 155–156, 600/158
See application file for complete search history.

(56) References Cited

U.S. PATENT DOCUMENTS

| | | | |
|---|---|---|---|
| 3,835,842 A | 9/1974 | Iglesias | |
| 3,900,022 A | 8/1975 | Widran | |
| 4,517,977 A | 5/1985 | Frost | |
| 5,085,658 A | 2/1992 | Meyer | |
| 5,320,091 A | 6/1994 | Grossi | |
| 5,392,765 A | 2/1995 | Muller | |
| 5,441,503 A | 8/1995 | Considine | |
| 5,486,155 A | 1/1996 | Muller | |
| 5,536,234 A * | 7/1996 | Newman | 600/104 |
| 5,605,545 A | 2/1997 | Nowosielski | |
| 5,807,240 A | 9/1998 | Muller | |

(Continued)

FOREIGN PATENT DOCUMENTS

| | | |
|---|---|---|
| DE | 196 33 124 A1 | 5/1997 |
| WO | WO 96/11638 | 4/1996 |
| WO | WO 99/11184 | 3/1999 |
| WO | WO 2006/021872 A2 | 3/2006 |

*Primary Examiner* — Matthew J Kasztejna
(74) *Attorney, Agent, or Firm* — Dickstein Shapiro LLP

(57) ABSTRACT

A continuous flow irrigation endoscope and a continuous flow irrigation fluid management system, both designed to be compatible to each other and meant to function as a single system. The endoscope and the fluid management system are synergistic to each other such that both enhance the efficiency of each other. The system allows a body tissue cavity to be distended by continuous flow irrigation so that the detached tissue pieces and waste fluid present inside a body tissue cavity are continuously automatically evacuated from the tissue cavity without causing the cavity to collapse at any stage and without the need of withdrawing the endoscope or a part of the endoscope from the tissue cavity.

14 Claims, 7 Drawing Sheets

(56) References Cited

U.S. PATENT DOCUMENTS

| | | |
|---|---|---|
| 6,030,359 A | 2/2000 | Nowosielski |
| 6,110,127 A | 8/2000 | Suzuki |
| 6,159,209 A | 12/2000 | Hakky |
| 6,645,140 B2 | 11/2003 | Brommersma |
| 6,824,544 B2 | 11/2004 | Boebel |
| 7,150,713 B2 | 12/2006 | Shener |
| 7,249,602 B1 | 7/2007 | Emanuel |
| 7,597,662 B2 | 10/2009 | Litscher |
| 2003/0130565 A1 | 7/2003 | Muller |
| 2003/0181906 A1 | 9/2003 | Boebel |
| 2006/0041186 A1 | 2/2006 | Vancaillie |
| 2006/0047185 A1 | 3/2006 | Shener |
| 2006/0122459 A1 | 6/2006 | Aue |
| 2006/0122557 A1 | 6/2006 | Kumar |
| 2008/0154095 A1 | 6/2008 | Stubkjaer |

* cited by examiner

EFFICIENT CONTINUOUS FLOW IRRIGATION SYSTEM

CROSS-REFERENCE TO RELATED APPLICATIONS

This is a divisional of application Ser. No. 11/871,051, filed on Oct. 11, 2007, now U.S. Pat. No. 8,226,549 which claims the benefit of Indian Provisional Patent Application No. 2235/DEL/2006, filed on Oct. 11, 2006, the entire disclosures of which are incorporated by reference herein.

FIELD OF THE INVENTION

The present invention relates to surgeries and, in particular, to endoscopic procedures which deploy continuous flow irrigation, such as transuretheral resection of the prostate/bladder, hysteroscopic procedures such as endometrial resection, fibroid resection, polyp resection, septoplasty, adhesiolysis and arthroscopic procedures.

BACKGROUND OF THE INVENTION

Continuous flow endoscopes are frequently used in endoscopic procedures such as hysteroscopy, trans uretheral urologic endoscopic procedures and arthroscopy. Those skilled in the art would know the structural composition of a continuous flow irrigation endoscope. In this application, the term "continuous flow irrigation" means that fluid simultaneously enters and escapes from a tissue cavity via separate entry and exit points, as a result of which positive fluid pressure is created inside the tissue cavity which distends the cavity.

A typical continuous flow irrigation endoscope comprises an inner sheath which is placed inside the cylindrical lumen of an outer sheath. The sheaths are hollow cylindrical tubes which have a distal end which enters a tissue cavity and a proximal end on which an inflow or outflow port is attached for the purpose of instilling or evacuating fluid from the cavity. The irrigation fluid is instilled via an inflow port. In many prior art systems, the instilled fluid travels through the lumen of the inflow sheath and enters the tissue cavity via the distal opening of the inflow sheath. The waste fluid present inside the tissue cavity enters into a potential space present between the outer and the inner sheaths via multiple holes present near the distal end of the outer sheath and this waste fluid is finally evacuated via the outflow port attached at the proximal end of the outer sheath. A fiber optic telescope is placed inside the cylindrical lumen of the inner sheath in order to view the interior of the tissue cavity. An endoscopic instrument, such as a wire loop electrosurgical cutting loop, is also placea in the lumen of the inner sheath. The positions of the outer sheath, the inner sheath and the telescope remain fixed with respect to each other. However, the electrosurgical cutting loop is capable of moving in a to and fro direction by virtue of which prostate tissue and uterine endometrial tissue is resected. The to and fro movement of the cutting loop is made by attaching the same to an externally located resectoscope.

In the arrangement described in the preceding paragraph, detached tissue pieces, larger than a critical size, present in the tissue cavity are unable to pass through the potential space between the outer and the inner sheaths. Thus, in endoscopic procedures such as endometrial resection and prostate resection, the entire endoscope or the "endoscopic instrument" has to be intermittently removed from the tissue cavity during the surgery to evacuate the detached tissue pieces present inside the tissue cavity, and this increases the risk of complications like perforation, excessive bleeding and also increases the surgical time. Let it be assumed that the positions of the inflow and outflow port are reversed which implies that the inflow port would be attached to the outer sheath while the outflow port would be attached to the inner sheath. Let it be further assumed that the inner lumen diameter of the outflow port is equal to the lumen diameter of the inner sheath. It could be argued that, in such an arrangement, detached tissue pieces and waste fluid would both be easily evacuated through the wide inner sheath and through the wide bore outflow port. However, such an arrangement could also cause the pressurized irrigation fluid present inside the tissue cavity to be expelled via the wide bore outflow port. This, in turn, could cause the tissue cavity to intermittently collapse during a surgical procedure, which in turn could lead to complications such as perforation and bleeding. It is for these reasons that the lumen diameter of the outflow port, in the prior art systems, is kept as less as possible. The system of the proposed invention solves the problems described in this paragraph despite the outflow port having a relatively large lumen diameter.

OBJECT OF THE INVENTION

An object of the invention is to provide a continuous flow irrigation system, comprising a resectoscope-based endoscope and a fluid management system, in which the detached tissue pieces present inside a tissue cavity are evacuated automatically in a continuous manner from the tissue cavity, without removing the resectoscope from the tissue cavity and without causing the tissue cavity to collapse at any given moment of time.

Another object of the invention is to provide a continuous flow irrigation resectoscope system, in which both the detached tissue pieces and waste fluid are simultaneously evacuated automatically in a continuous manner from the tissue cavity via a same single outflow port attached to the inner sheath.

Another object of the invention is to provide a continuous flow irrigation resectoscope in which the evacuation of the detached tissue pieces is enhanced by making the diameter of the lumen of the round outflow port at least equal to the diameter of the inner sheath.

Another object of the invention is to provide a continuous flow irrigation resectoscope in, which the evacuation of the detached tissue pieces is further enhanced by incorporating an outflow port having an elliptical lumen with the short axis being at least equal to the diameter of the inner sheath.

Another object of the invention is to provide a continuous flow irrigation system in which the evacuation of the detached tissue pieces is enhanced by attaching an outflow tube having an elliptical cross section to an outflow port having an elliptical lumen.

Another object of the invention is to provide a continuous flow irrigation system which is user friendly, safe and efficient.

BRIEF SUMMARY OF THE INVENTION

The present invention provides s continuous flow irrigation endoscope and a continuous flow irrigation fluid management system. The endoscope and fluid management system are both designed to be compatible to each other and function as a single system. The endoscope and the fluid management system are synergistic to each other such that both enhance the efficiency of each other. The invented system allows a body tissue cavity to be distended by continuous flow irrigation so that the detached tissue pieces and waste fluid present inside a body tissue cavity are continuously automatically evacuated without causing the cavity to collapse at any stage and without the need of withdrawing the endoscope of a part of the endoscope from the tissue cavity.

The endoscope comprises an inner sheath placed inside an outer sheath. An outflow port having a lumen diameter at least equal to the lumen diameter of the inner sheath is located near the proximal end of the inner sheath. Fluid is instilled via an inflow port located near the proximal end of the outer sheath and such fluid enters a potential space between both the sheaths which serves as the inflow channel for instilling sterile irrigation into a tissue cavity. The inner sheath serves as a conduit for evacuating waste fluid and detached tissue pieces present inside a tissue cavity via the outflow port.

The fluid management system comprises an inflow pump and an outflow pump (for example, an inflow peristaltic pump and an outflow peristaltic pump) which work simultaneously, for indefinite time, at fixed flow rates to create and maintain any desired cavity pressure for any desired cavity flow rate. The inflow pump is connected to the inflow port of the endoscope via an inflow tube, while the outflow pump is connected to the outflow port of the endoscope via the outflow tube.

DETAILED DESCRIPTION OF THE INVENTION

The system of the present invention comprises an endoscope, preferably a resectoscope based endoscope, and a fluid management system, both designed especially for each other. The endoscope and the fluid management are both based on the principles of continuous flow irrigation, as both work together as one unit to evacuate detached tissue pieces and waste fluid from a tissue cavity in endoscopic procedures which deploy continuous flow irrigation and without the necessity of withdrawing the endoscope or a part of the endoscope from the tissue cavity.

For easy understanding, the endoscope and the fluid management system shall be described separately, followed by a description of both of them together.

The Endoscope

The present invention relates to a continuous flow irrigation endoscope, preferably a resectoscope based endoscope, in which detached tissue pieces and waste fluid present inside a tissue cavity are automatically evacuated in a continuous manner without withdrawing the endoscope or any part of the endoscope from the tissue cavity.

Figure 2:
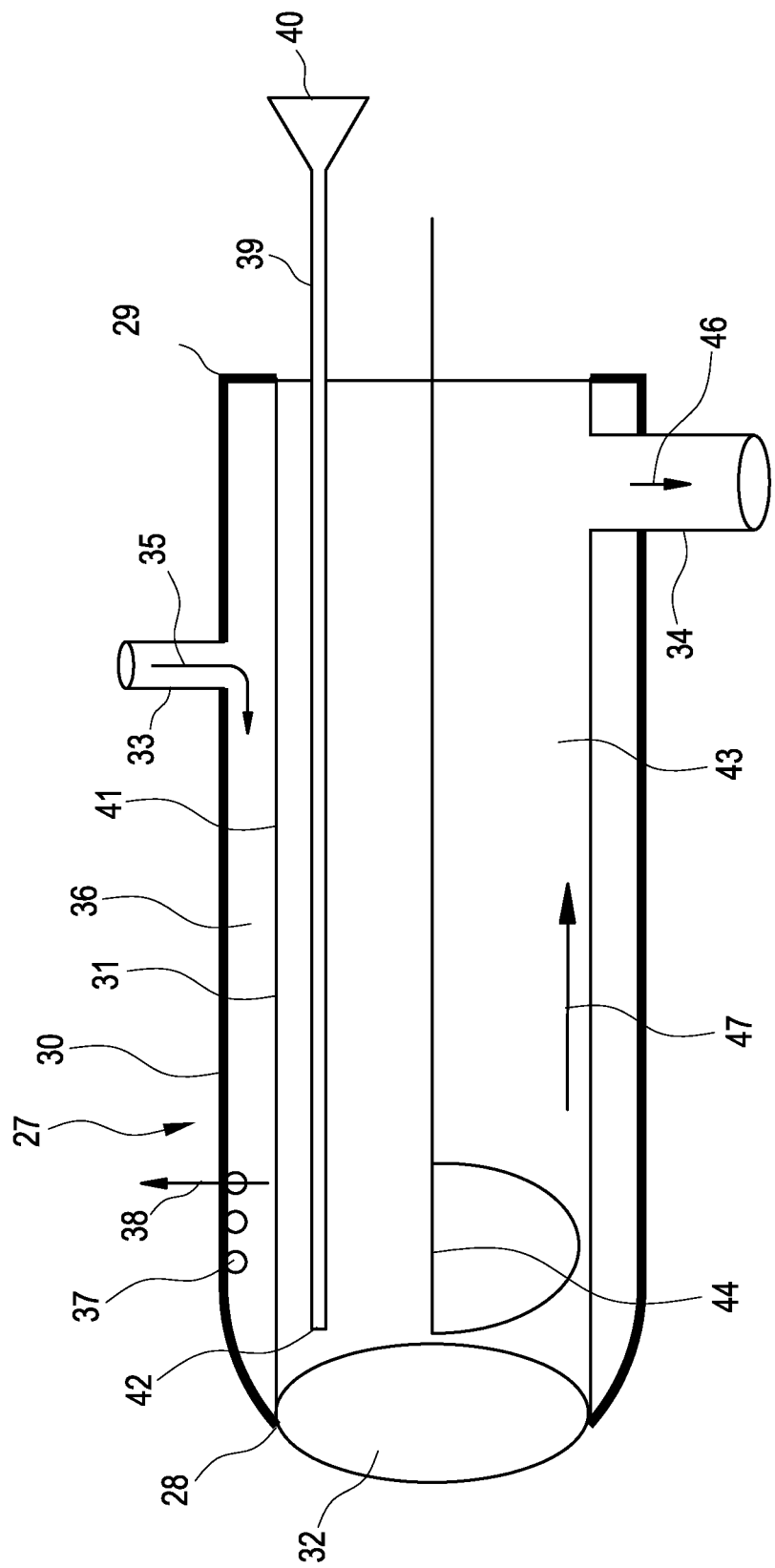
FIG. 2 shows the endoscope of FIG. 1.

The basic layout of the endoscope of the present invention is shown in FIG. 2. The endoscope 27 has a distal end 28 which enters a tissue cavity and a proximal end 29 which lies outside the tissue cavity. The endoscope comprises an outer sheath 30 and an inner sheath 31. Near the distal end, the outer sheath 30 is shown to be having a tapering end such that distal most edge of the outer sheath 30 touches the inner sheath 31 making a fluid tight contact with the same. Such an arrangement is made to create a closed cavity between the outer and the inner sheaths, and such closed space shall be termed as "potential space" in subsequent paragraphs. Alternatively, the distal end of the outer sheath may not be tapered, and instead the distal end of the inner sheath may be thickened, such as in the form of a ceramic beak or otherwise. However, such arrangement is not shown in any figure.

Again referring to FIG. 2, the outer and the inner sheaths have a round opening each at their distal ends but since the inner and the outer sheaths touch each other at their distal most ends a single opening 32 is being drawn to represent the openings of both the sheaths. The outer sheath 30 has an inflow port 33 located near the proximal end 29. The inner sheath 31 has an outflow port 34. It is important to note that the cross sectional diameter of the outflow port is preferably about equal to the cross sectional diameter of the inflow sheath 31 which is further about equal to the cross sectional diameter of the opening 32. The cross sectional diameter of the outflow port could also be less than about the cross sectional diameter of the inflow sheath 31 but such an arrangement could retard the evacuation of the detached tissue pieces through the out flow port 34.

Sterile irrigation fluid meant for distending a body tissue cavity is instilled via the inflow port 33 in the direction of the arrow 35. The irrigation fluid travels through the closed "potential space" 36 between the outer and the inner sheaths and finally enters the tissue cavity via multiple openings 37 located near the distal end of the outer sheath 30. The irrigation fluid entering the tissue cavity is denoted by arrow 38. The openings 37 have been denoted by three circles only for the sake of easy illustration. The openings could be multiple in number and they could also be in the form of longitudinal slits or of any other shape. The cross section of the distally located opening 32 could also be oval in shape, or may have any other desired configuration, depending upon the surgical requirement.

Again referring to FIG. 2, the optical system 39 comprises a "telescope eyepiece" 40 which is connectable to a video camera, an "optical channel" 41 which contains fiber optic bundles and a "distal viewing tip" 42 for visualizing the interior of the tissue cavity. The optical channel 41 is placed inside the lumen 43 of the inner sheath 31. The optical channel is about parallel to the inner sheath 31 and the outer sheath 30. The entire optical system 39 along with the optical channel 41 is preferably fixed relative to both the sheaths. Also the optical channel 41 enters the inner sheath 31 by virtue of a fluid tight contact. The optical channel could also be bent at an appropriate locate, however such arrangement has not been shown in any of the drawings only to keep the drawings simple.

Again referring to FIG. 2, an electrosurgical wire loop electrode 44 has also been placed inside the lumen 43 of the inner sheath 31. The wire loop 44 enters the inner sheath 31 by virtue of a water tight contact. The wire loop electrode cuts tissue by moving in a to and fro direction relative to the long axis of both sheaths 30 and 31. The to and fro movement is achieved by virtue of the electrode 44 being attached to an externally located resectoscope not shown in any of the drawings. The wire loop electrode 44 could also be replaced by "another endoscopic instrument" such as a roller ball electrode, a right angle electrode, a myoma screw, a knife, a forceps or a scissor, for example. The "another endoscopic instrument" could also be capable of rotating around its long axis.

Again referring to FIG. 2, the waste fluid which is present inside the tissue cavity and the detached tissue pieces present inside the cavity enter via the opening 32 move in the direction of the arrow 47 inside the lumen 43 of the inner sheath and are finally evacuated via the outflow port 34 in the direction of the arrow 46. The outflow port 34 instead of being attached at right angle to the inner sheath 31 could also be preferably attached in an oblique direction, so that the outflow port and the distal length of the inner sheath form an obtuse angle. The outflow port could even be parallel to the long axis of the inner sheath 31, if mechanical constraints permitted and such arrangements could further facilitate the evacuation of detached tissue pieces. Generally, the "detached tissue pieces" are created resultant to electrosurgical procedures such as endometrial resection, fibroid resection and prostate resection.

Also, those skilled in the art would know that, generally, an obturator is inserted in the outer sheath subsequent to which the outer sheath is inserted into a tissue cavity. However, the obturator assembly has not been included in the drawings only for the sake of simplicity.

Referring to FIG. 2, the relative locations of the optical channel 41 and the wire loop electrode 44 could even be interchanged with respect to the outflow and the inflow ports.

Referring to FIG. 2, the lumen diameter of the out flow port 34 and the inflow sheath 31 being substantially large in magnitude could cause the pressurized irrigation fluid present inside a tissue cavity to be intermittently expelled via the large bore outflow port 34. This would cause the tissue cavity to intermittently collapse during an endoscopic procedure, which could lead to surgical complications like perforation and bleeding. In order to solve this problem, it is recommended that the endoscope 27 be used with a specially designed fluid management system which would not allow the tissue cavity to collapse and would also provide additional benefits. Such a fluid management system is described in the subsequent paragraphs.

The shape of the lumen of the outflow port can also be oval in shape, for example, elliptical, wherein the small axis of the lumen of the outflow port could be made equal to the radius of the inner sheath and the long axis obviously would be more than the radius of the inner sheath. A round lumen always has a smaller area of cross section compared to an elliptical lumen having a short axis equal to the radius of the round lumen. The area of cross section of a circle is $\pi \times radius^2$ (wherein $\pi$ is pi) and the area of cross section of an ellipse is "$\pi \times short\ axis \times long\ axis$." As noted, on account of having a relatively greater area of cross section, an elliptical outflow port evacuates detached tissue pieces more efficiently compared to a round outflow port whose radius equal to the short axis of the said elliptical outflow port. In accordance with the current discussion in case the outflow port 34 were to be elliptical in cross section, then the outflow tube 12 should also preferably have an elliptical cross section, the short and long axis being similar for both. Such arrangement is beneficial because it enhances the passage of detached tissue pieces through the outflow tube. An arrangement wherein an elliptical outflow port is attached to an elliptical outflow tube is more efficient than an arrangement wherein a round outflow port is attached to a round outflow tube (assuming the short axis of the ellipse is about equal to the radius of the outflow port, and both being equal to the radius of the lumen of the inner sheath). The arrangement of the elliptical outflow port attached to an elliptical outflow tube is relatively more efficient because relatively more number of detached tissue pieces can be accommodated side by side inside the elliptical lumen which has relatively greater area of cross section.

The Fluid Management System

The "fluid management system" described below is recommended to be used with the endoscope described in the previous paragraphs. The fluid management system is a system for distending body tissue cavities in endoscopic procedures. The proposed fluid management system distends a body tissue cavity by continuous flow irrigation so that the cavity pressure is absolutely independent of the cavity outflow rate, such the both the cavity pressure and the outflow rate may be independently altered without varying the value of the other parameter. For brevity, the "fluid management system" shall be referred to as "system."

Figure 1:
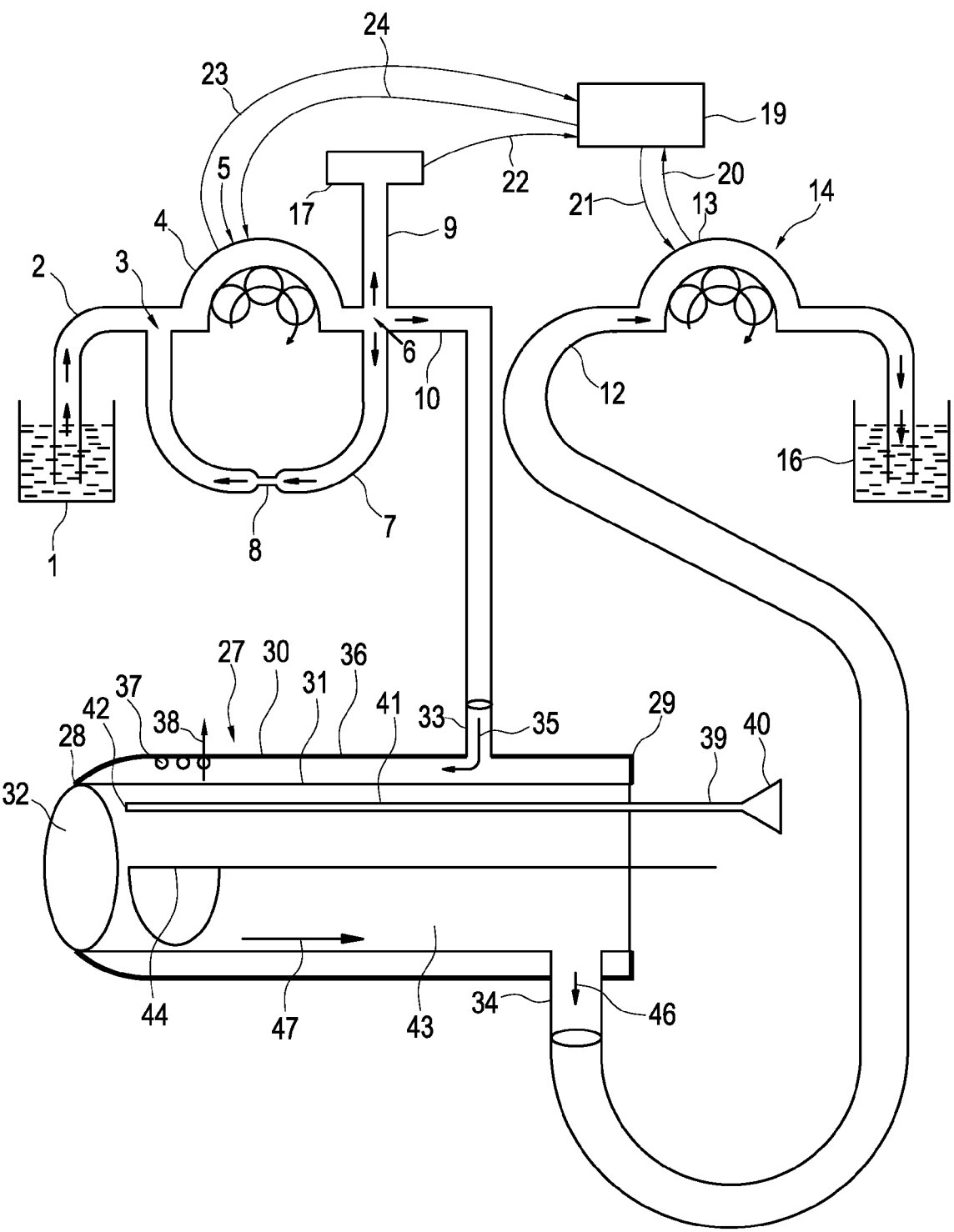
FIG. 1 illustrates the system of the present invention comprising an endoscope attached to a fluid management system.
Figure 3:
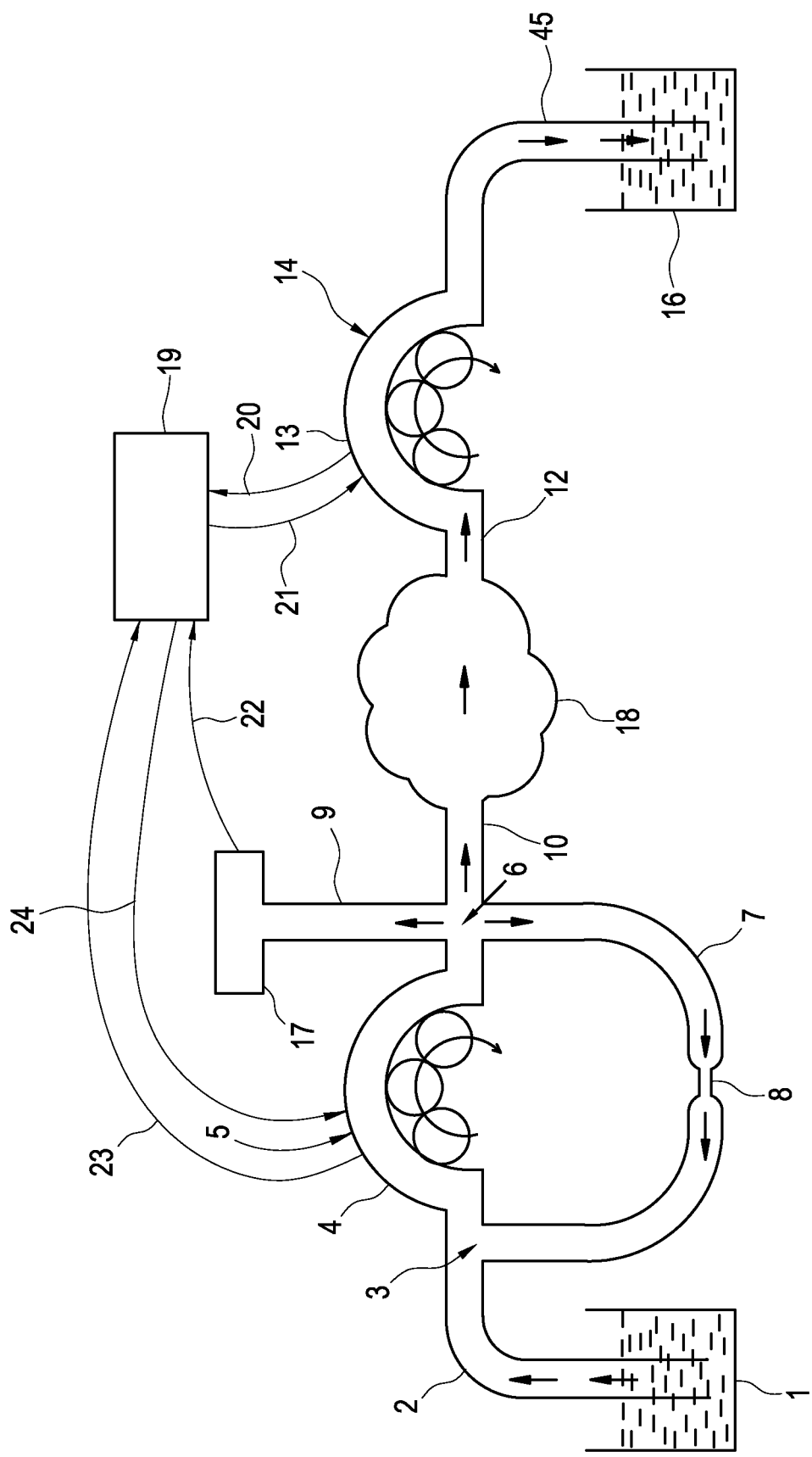
FIG. 3 is similar to FIG. 1, except that, in this figure, a tissue cavity has been substituted in place of the endoscope.
Figure 4:
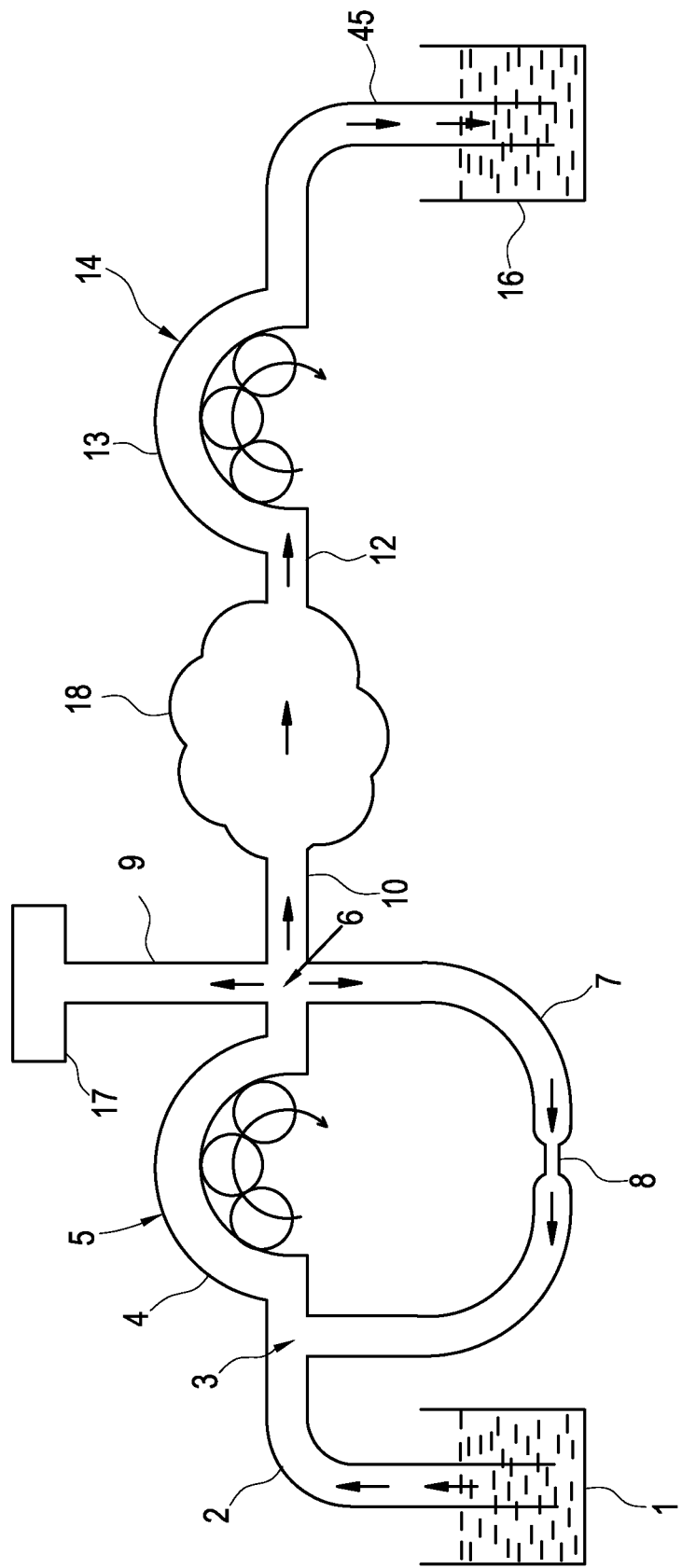
FIG. 4 is similar to FIG. 3, except that, in this figure, a controller is not included.

The schematic diagram of the system is shown in FIG. 3. Two peristaltic pumps 5 and 14 operate simultaneously to distend a tissue cavity so that the cavity pressure is totally independent of the cavity outflow rate. FIG. 3 represents the complete schematic diagram of the "system." The controller being used in the system shown in FIG. 1 is an optional feature and the system would provide most of the features even without the controller. FIG. 4 represents the schematic diagram of the system but without a controller system. Thus, FIG. 4 is a mechanical version of the system. A human operator is required to operate such mechanical version of the system shown in FIG. 4. Though it is recommended that the controller based version of the system be used in endoscopic surgeries, it is not essential. The controller being used in the present system merely assists the user in arriving easily at some of the additional functions which otherwise can be performed manually. Thus, in this application, the mechanical version of the system shown in FIG. 4 is being discussed in more detail to explain the basic physical principals of the system with a greater clarity.

Referring to FIG. 4, the system shown in this figure comprises two peristaltic pumps which can maintain a predictably precise stable cavity pressure for indefinite time by working simultaneously at constant rotational speeds. Pump 5 pushes fluid into the cavity 18 and while pump 14 simultaneously extracts fluid out of the cavity 18. The inlet end of the inflow peristaltic pump 5 is connected to a fluid source reservoir 1 via tube 2. The distal open end of tube 2 is constantly submerged in a sterile non viscous physiological fluid like 0.9% normal saline, 1.5% glycine, ringer lactate or 5% dextrose contained inside the reservoir 1 at atmospheric pressure. One end of the tube 7 connects the 'T junction' 3 situated at the inlet end of the pump 5 while the other end of tube 7 connects with the 'square junction' 6 situated at the outlet end of the pump 5. The 'T' junction 3 is thus the meeting point of three tubes, namely 2, 4 and 7. Similarly the square junction 6 is the meeting point of four tubes 4, 9, 7 and 10. The rollers of the peristaltic pump 5 continuously compress and roll over the entire length of tube 4 thus displacing fluid in the direction of the curved arrow. This curved arrow denotes the direction in which the rotors of the peristaltic pump 5 rotate. Tube 7 has a constriction point 8 which can be located anywhere along its length. Such constriction point refers to a point where the inner diameter of the lumen of tube 7 is reduced in comparison to the lumen of the rest of the tube 7. Such constriction may be a permanent constriction in the lumen of tube 7 or it may be a variable constriction whose diameter may be increased or decreased as desired. A pressure transducer 17 is attached at one of tube 9 while the other end of tube 9 is connected anywhere on inflow tube 10. For practical convenience, it is desirable that the other end of tube 9 be connected in the up stream part of the inflow tube 10 such as at the square junction 6. The pressure transducer 17 measures the fluid pressure via a column of liquid or air present in the lumen of tube 9. The fluid pressure as measured by the pressure transducer shall be referred to as P. In this application, the term "P" refers to the actual pressure inside the tissue cavity but in physical terms P is the pressure sensed by the transducer 17 at point 6. The pressure transducer 17 may also be in the form of a membrane diaphragm incorporated in the wall of the inflow tube 10 such that this membrane diaphragm is in direct contact with the fluid contained in the inflow tube 10, such that the linear movement excursions of the said membrane are interpreted as pressure of the fluid inside the inflow tube 10 by a suitable pressure transducer. Such type of pressure sensor being directly incorporated in the wall of the inflow tube 10 senses the fluid pressure without the intervention of tube 9. The basic purpose of the transducer is to measure the fluid pressure inside the inflow tube 10, such as at point 6, thus the mechanical construction of the transducer is not important as long as it measures the fluid pressure.

For simplicity, the existence of tube 9 shall be continued to be considered in the rest of the application. The peristaltic pump 14 attached to the outflow side actively extracts fluid out of the tissue cavity 18 via the out flow tube 12. The outlet end of the pump 14 is connected to a waste fluid carrying tube 45 which opens into a waste fluid collecting reservoir 16 at atmospheric pressure. The rollers of the pump 14 constantly compress and roll over the entire length of the peristaltic pump tubing 13 thus displacing fluid in the direction of the curved arrow which also corresponds with the direction of pump rotation.

In order to understand the system in a simpler manner, both pumps are being considered to be identical in all respects and all the tubes are also being considered to be having the same uniform inner diameter. However, the inner diameter of the tubes could also be different. Tubes 4 and 13 consist of a soft resilient plastic material which can be efficiently compressed by the rollers of the peristaltic pumps. The other tubes also consist of a suitable resilient plastic material. It is assumed that all the components shown in FIG. 4, including the two pumps, all tubes and the said cavity, are placed at the same horizontal height with respect to the ground. Also, the rollers of pumps 5 and 14 should press adequately over tubes 4 and 13 in such a manner that there is no leak through these tubes when the pumps are stationary. It is also assumed that there is no abnormal leak of fluid in the irrigation system, for example leak via a accidental hole made in any irrigation tube or a fluid leak which might occur if the endoscope loosely enters into the tissue cavity, for example in hysteroscopic surgery fluid leaks by the sides of the endoscope if the cervix is over dilated.

Figure 7:
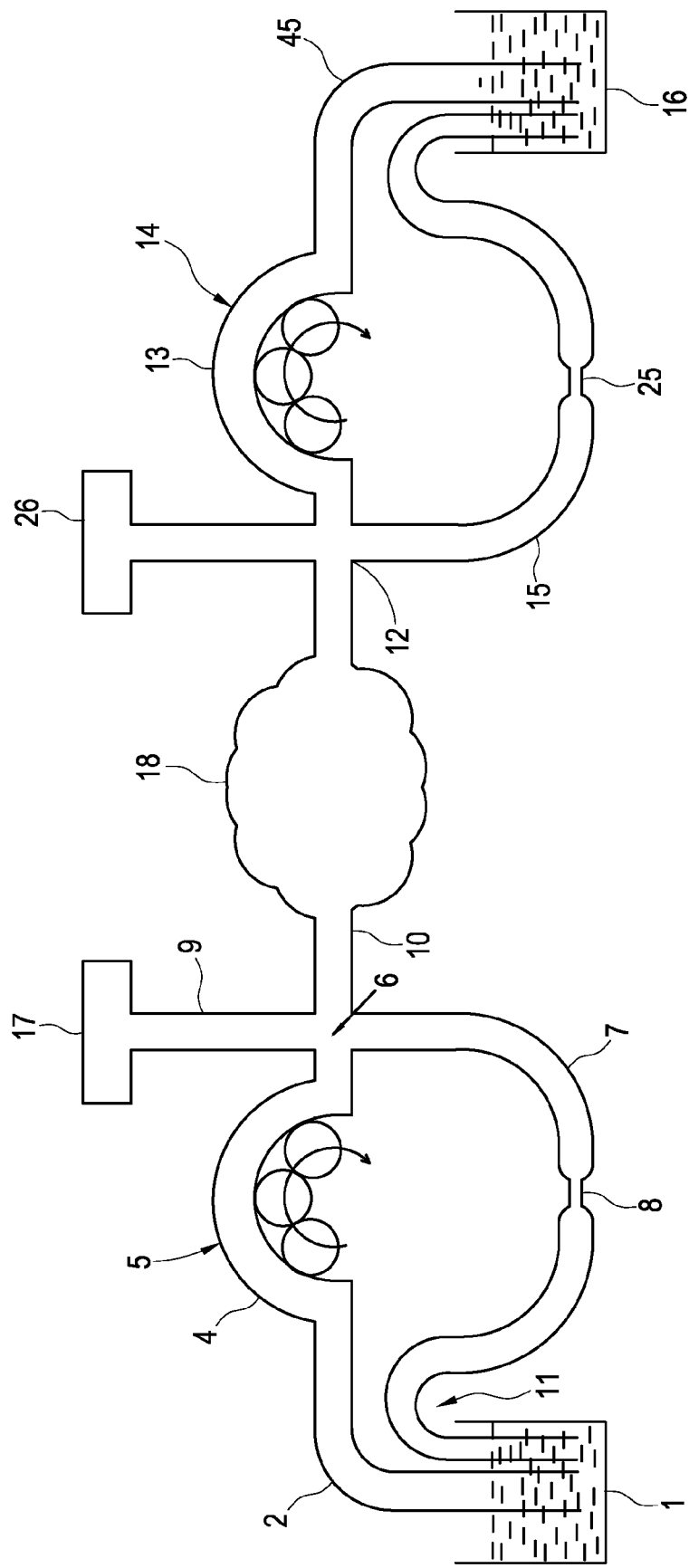
FIG. 7 is similar to FIG. 2, except that, in this figure, an additional/optional constriction site housing tube 15 and an additional/optional pressure transducer 26 have been included.

One end of the constriction site housing tube 7 instead of being connected with tube 2 at the 'T' junction 3 can also open directly into the fluid source reservoir 1. This shall not affect the efficiency of the system in any way but it may be practically difficult from the surgical point of view in some special cases. Thus, such a provision is separately shown in FIG. 7 and the tube has been labeled as 11 but it has intentionally not been included in the main block diagram of the system as in FIGS. 3 and 4 in order to keep the drawings simple. Also, a constriction site housing tube similar to tube 7 labeled as 15 can be attached to the outflow tube 12 as shown in FIG. 7. In the tube 15, the constriction site is labeled as 25. Such tube can serve a number of purposes. Tube 15 can be utilized for relatively faster evacuation of air bubbles from the cavity. In place of the adjustable constriction site 25, a pressure release safety valve may be incorporated as a safety feature, however it is more beneficial to install such pressure safety valve in the inflow circuit. The tube 15 may also be used for quickly flushing air bubbles from the irrigation tubes by fully opening the constriction site 25 for a few minutes or seconds. The tube 15 may also be used for any other purpose as deemed fit by the surgeon. However, the tube 15 has intentionally not been included in the main block diagrams of the system because by including the tube 15 in the main block diagrams it would have become very difficult to explain the basic physical principals of the system. However, tube 15 is a very beneficial component and is thus recommended to be incorporated in the system. The opening and closing of the constriction, site 25 can also be regulated manually to help in various special advanced endoscopic applications. Incorporation of tube 15 with the variable constriction site 25 can help in reducing the substantially high amplitude pressure variations inside the cavity caused by abnormally large cavity wall contractions, but such phenomenon is only rarely encountered. Also, an additional pressure transducer 26 may also be attached on the out flow tube 12, if desired, as shown in FIG. 7. However the said pressure transducer 26 has intentionally not been included in the main block diagrams of the system because by doing so it would have become very difficult to explain the basic physical principals of the system.

Figure 5:
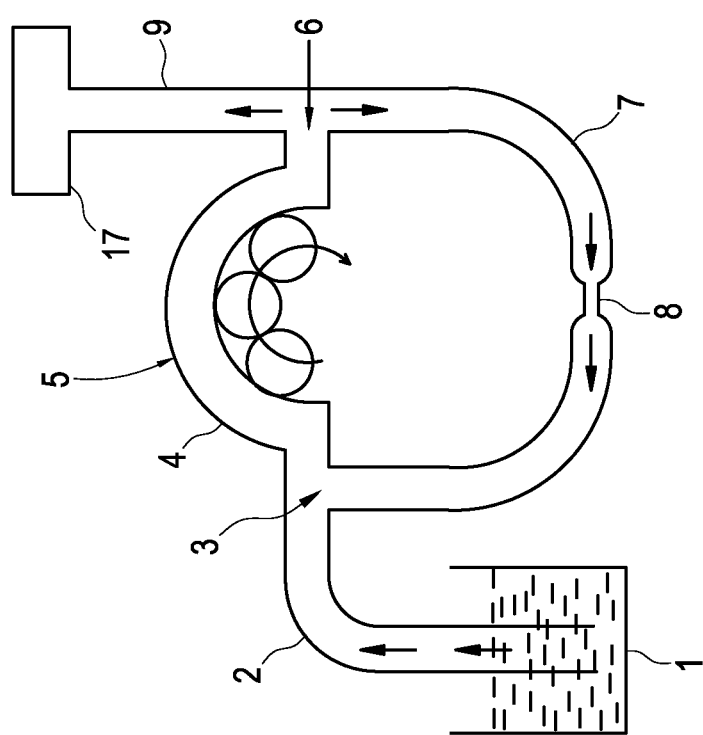
FIG. 5 shows the inflow part of the fluid management system along with the inflow peristaltic pump 5, the pressure transducer 17 and the constriction site 8.

In order to clearly understand the system shown in FIG. 4, it would be helpful to discuss the functioning of the inflow peristaltic pump 5 as a separate entity as shown in FIG. 5. The rollers of pump 5 move in the direction of the curved arrow and squeeze over the entire length of peristaltic pump tubing 4. Initially tubes 2, 4, 7 and 9 contain air at atmospheric pressure and the free open end of tube 2 is submerged in a sterile fluid contained inside the fluid source reservoir 1. The moment the constriction site 8 is fully occluded a column of fluid is immediately sucked into tube 4 via tube 2, and thus fluid starts accumulating in the proximal parts of tubes 9 and 7. As the fluid fills in tube 9, it pushes a column of air distal to the fluid column created in tube 9 and the pressure of this compressed air column is sensed by the pressure transducer 17. The fluid pressure and the pressure of the compressed air column are same, thus the pressure transducer 17 actually senses the fluid pressure. If tube 7 continues to remain fully occluded at the constriction site 8, the fluid continues to accumulate inside tubes 9 and in that part of tube 7 which lies between point 6 and the constriction site 8, and the pressure transducer 17 thus displays a continuously rising fluid pressure. The moment the block at the constriction site 8 is partially released the fluid escapes in the form of a jet through the partially open constriction opening 8 in the direction of point 3. With the constriction opening 8 being only partially blocked, if the pump 5 continues to rotate at a constant rotational speed, the fluid pressure ultimately gets stabilized at a fixed value provided the internal diameter of the constriction site 8 is not further varied.

The diameter D of the constriction site 8 ranges from a minimum non-zero value to a maximum value which is less than the overall diameter of the rest of the housing tube. Thus, in this application, the inner diameter of the constriction site 8 shall be deemed to be fixed at some predetermined value D, unless otherwise stated. The fluid being displaced by the peristaltic pumps is actually pulsatile in nature thus the fluid pressure exhibits minute pulsations having a fixed frequency and a fixed amplitude. From the practical point of view, such minute pressure fluctuations of such a regular nature can be ignored in context with distension of body tissue cavities in endoscopic procedures. Thus, in the entire application, the fluid pressure shall be assumed to be non-fluctuating in nature.

Figure 6:
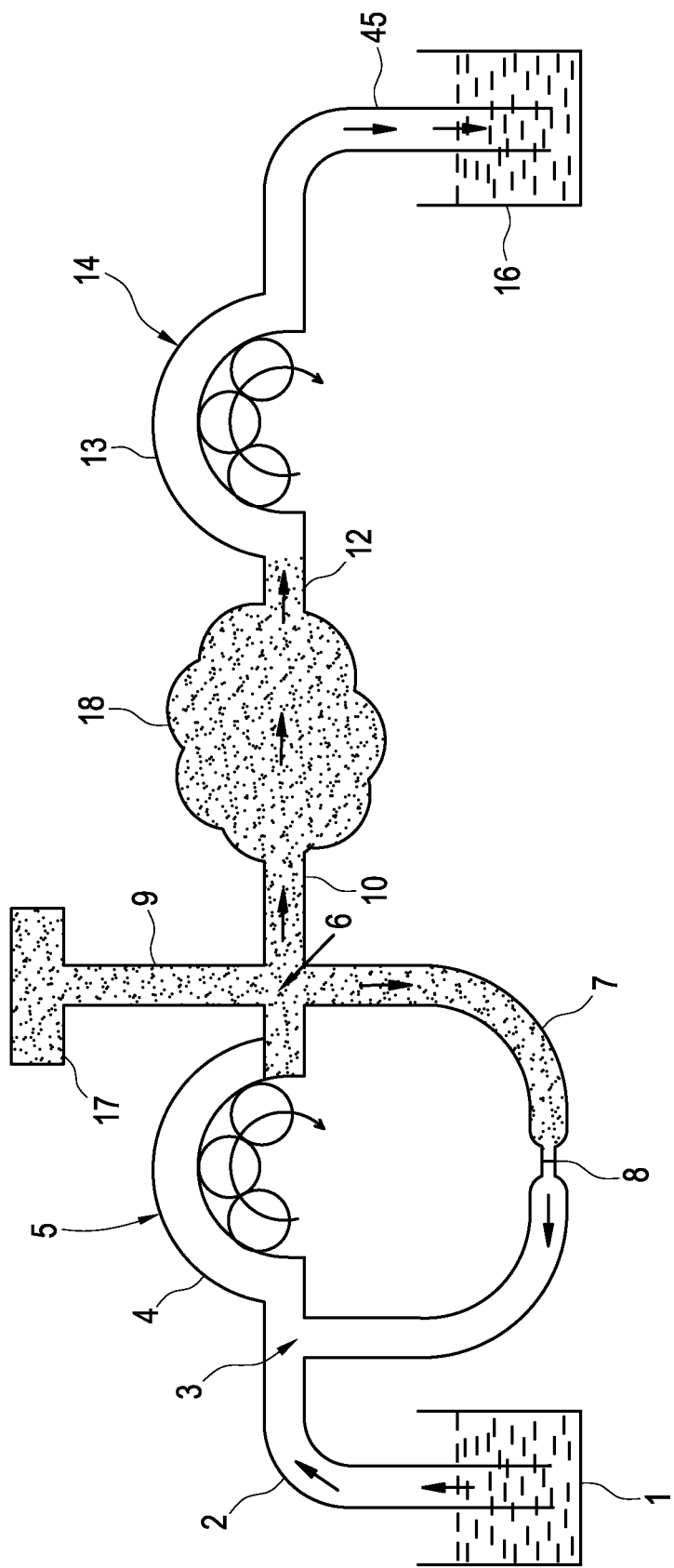
FIG. 6 is similar to FIG. 4, except that, in this figure, a shaded area represents a region having an almost similar pressure.

Referring to FIG. 6, this figure is similar to FIG. 4 but a limited region of the irrigation circuit having an almost same pressure has been shaded black. Due to frictional resistance experienced by the moving fluid the pressure at point 6, as sensed by the transducer 17, is always found to be higher than the actual pressure inside the tissue cavity 18 but the pressure difference is so small that it may be neglected from the practical surgical point of view. Also, such pressure difference increases as the fluid flow rate increases. The term "out flow rate" being referred to the flow rate of pump 14. Also, the pressure difference remains constant all through surgery at any fixed outflow rate. Though the pressure difference is negligible but if desired its effect can also be totally negated by subtracting its value from the pressure reading of the transducer. In this manner, in endoscopic surgeries, it is possible to determine the actual cavity pressure by using the pressure transducer 17 located far away from the cavity. This feature is of special relevance because in endoscopic procedures like hysteroscopy, arthroscopy and brain endoscopic surgery where it is important to know the actual cavity pressure but at the same time it is practically difficult to take a pressure measurement directly from the cavity.

Referring to FIG. 4, it shall be first described as to how the "system" can be used mechanically, that is without a controller. The peristaltic pumps 5 and 14 can be made to work at any fixed rotational speed and the fluid flow rate of each pump is directly proportional to the pump RPM or the pump rotational speed. Thus, any precise pump flow rate can be generated by selecting a suitable pump rotational speed. The fluid flow rate of pump 14 shall henceforth be denoted by R2 and shall be termed as the "outflow rate." The fluid flow rate of pump 5 shall be denoted by R1 and shall be termed as the "inflow rate." It is noted that the term 'inflow rate' R1 is not the true inflow rate for the cavity 18, as might be suggested by the literary meaning of the term 'inflow' because R1 is not the actual rate at which fluid into the cavity 18 because some fluid also constantly escapes through the constriction site opening 8. Henceforth, the term 'inflow rate' shall only be referred to the flow rate of the inflow pump 5 unless specifically mentioned. However, the term 'outflow rate' R2 does correspond to the literary meaning of the term 'outflow' because R2 is equal to the rate at which fluid flows out of the cavity 18. The surgeon initially decides an out flow rate R2 by selecting a suitable rotational speed for pump 14. Next, the surgeon decides the maximum flow rate at which fluid could be allowed to enter into the cavity via the inflow tube 10 and the inflow pump 5 is set to work at such flow rate or at a flow rate slightly lesser than this. Intravasation is process by which fluid enters into the patient's blood circulation through the cut ends of blood vessels located in the cavity wall or enters into the patient's body, for example into the peritoneal cavity, as a result of an accidental perforation or escapes via patent fallopian tubes into the peritoneal cavity. Thus "intravasation" is a process by which the pressurized irrigation fluid enters into the patient's body system through the walls of the tissue cavity. In case of a surgical accident like cavity wall perforation the fluid being pumped by the inflow pump 5 can enter into the patient's body at a rate almost equal to R1. The maximum rate of fluid intravasation cannot exceed the value R1. In case of an accident like cavity wall perforation, it may take some time before an abnormally high intravasation rate is discovered and in such time a dangerous quantity of fluid might enter into the patient's body. If the inflow rate R1 is kept at a relatively lower value then the volume of intravasated fluid in case of such an accident would be low. After fixing the values for R2 and R1 the system is started and the diameter of the constriction site 8 is gradually reduced. As the diameter of the constriction site 8 is reduced, fluid starts flowing into the tissue cavity and the pressure inside the tissue cavity starts rising. When the desired pressure is achieved inside the tissue cavity, the diameter of the constriction site 8 is not reduced any further and is fixed. The diameter of the constrictions site at this stage is termed as "D." The constriction site may also be a plastic or metal piece which has a hole in the centre such that the diameter of the hole is permanently fixed at some value D. If a constriction 8 has a permanently fixed diameter then only the flow rates of pumps 14 and 5 have to be set before the system becomes completely operational.

The importance of incorporating the housing tube 7 with the constriction site and the non-obvious advantages provided by the housing tube 7 with the constriction site are detailed below.

The surgeons have only two options, either to ignore cavity pressure variations by not correcting them, or to externally and actively correct such pressure variations. To externally and actively correct the variations in the cavity pressure, controller is generally incorporated and the working of the pumps is essentially controlled by the controller. Incorporation of the controller controlling the operation of the pumps does not provide any benefit. The controller activates the controlling action after the variations in the cavity pressure have subdued. Thus, the controlling action initiated by the controller instead of benefiting the surgeon leads to an undesirable turbulence inside the cavity and also tends to amplify the resultant movement excursions of the cavity walls.

The inventors have noticed that, if the controller continuously controls the operations of the pumps (either on the inflow side or on the outflow side), the cavity pressure continuously fluctuates around a preset value and it is not possible to attain a constant value. The inventors believe that the controller provides proper corrective action (by continuously controlling the operations of the pumps) only if the fluctuations in the cavity pressure are gradual and not highly instantaneous. That is, if the quantitative rise/fall in the cavity pressure is over long time period, the controller would be able to provide proper corrective action. As the time period to detect variation in the cavity pressure and commence corrective action is ideally in the range of 2 to 4 seconds, if the quantitative rise/fall in the cavity pressure is over very short time period, the suggested mechanism of providing a controller will be unsuitable. Under such instances, instead of providing any corrective action, the controller destabilizes the system and induces additional pressure fluctuations inside the cavity (because of commencing a corrective action at a delayed stage). Thus, it takes very long time for the system to once again get stabilized.

The inventors have surprisingly found that incorporation of a housing tube provided with a constriction site at the inflow side, as described above, inherently and passively corrects the pressure variations due to physiological cavity wall contractions and the mechanical movement of the tubes and the endoscope and also limits the variation in the size of the cavity. The applicants highlight that it is important to control both the variations in the pressure inside the cavity and the changes in the size of the distended cavity. Large variations in the pressure inside the cavity or the size of the cavity are detrimental to the surgical procedure. During the contraction of the cavity, a minute quantity of the fluid is pushed out of the cavity. If during this stage the system does not provide a way for releasing the fluid being pushed out, the instantaneous pressure inside the cavity increases tremendously which is harmful to the patient. On the other hand, if the amount of fluid being pushed out of the cavity is not checked or controlled, the changes in the size of the distended cavity are very high. The incorporation of the housing tube having the constriction site in the present system controls both the variations in the pressure inside the cavity and the changes in the size of the distended cavity. The housing tube having the constriction site provides a by-pass route for the fluid being pushed out of the cavity to go back to the fluid supply tube or the fluid source reservoir. This avoids the instantaneous pressure surge inside the cavity which is harmful to the patient. The size of the diameter at the constriction site automatically controls the amount of fluid passing through the housing tube, thereby controlling the amount of fluid being pushed out of the cavity. Inclusion of the housing tube with the constriction site therefore minimizes the instantaneous variations in the size of the distended cavity.

Alternatively, if the cavity expands a suitable volume of fluid is sucked into the cavity from the irrigation circuit, such as from the region of point 6, and this is accompanied by a corresponding transient decrease in the flow rate at which fluid which fluid is escaping via the constriction site 8 in the direction of point 3 but if the magnitude of the physiological expansion is more fluid may even be sucked into the cavity via the constriction site 8. This implies that the constriction site 8 is helping in maintaining a stable cavity pressure despite physiological cavity wall contractions by suitably varying the magnitude of an imaginary fluid flow vector passing through the constriction site 8.

Determining the Real Time Rate of Fluid Intravasation

Referring to FIG. 4, let it be hypothetically assumed that the diameter at the constriction site 8 has been fixed at some predetermined value D, the outflow and the inflow rates have been fixed at some values R2 and R1 respectively and in such a situation a pressure P is created inside the tissue cavity 18 when the system is operated. In such case, if no intravasation occurs during the endoscopic procedure, then the pressure inside the tissue cavity 18 continues to remain at the same value P. However, if at any stage during the endoscopic procedure intravasation occurs, then the cavity pressure immediately falls below the desired initial value P and inflow rate has to be increased by some magnitude in order to raise the cavity pressure to its initial value P. Here magnitude of the required increase in the inflow rate to attain the initial cavity pressure P is equal to the instantaneous real time rate of intravasation R3 existing at that moment of time. In this way, the real time rate of fluid intravasation can be determined by using the mechanical version of the system.

Cavity Pressure or the Outflow Rate, Both can be Altered Independently without Varying the Value of the Other Parameter Referring again to FIG. 4, a hypothetical endoscopic procedure is being considered where surgery is being performed at an outflow rate R2 and inflow rate R1 with the constriction 8 diameter being been fixed at some value D and a resultant cavity pressure P being created maintained. In such hypothetical situation, as long as R2 and R1 are not altered, the cavity pressure P remains predictably constant throughout surgery resulting in a predictably stable mechanical distension of the tissue cavity walls which culminates in constant clear visualization throughout the endoscopic procedure. If in the hypothetical procedure the cavity pressure needs to be increased without altering the out flow rate R2, then all that is needed is to start increasing the value of R1 and stop doing so when the desired higher cavity pressure is achieved. Similarly, if the cavity pressure needs to be decreased without altering the out flow rate R2 then R1 is decreased till the desired lower cavity pressure is attained. In the hypothetical endoscopic procedure, if the outflow rate R2 needs to be increased without altering the cavity pressure P, then the value of R2 is increased by the desired magnitude but simultaneously the value of R1 is also increased by a similar magnitude. Similarly, if the outflow rate R2 needs to be decreased without altering the cavity pressure P, then the value of R2 is decreased by the desired magnitude but simultaneously the value of R1 is also decreased by a similar magnitude. Thus, if R1 and R2 are simultaneously increased or decreased by the same magnitude, the cavity pressure does not vary, the value D is always fixed as already stated.

The preceding statements shall now be explained by the help of a numerical hypothetical example. In reference to FIG. 4, considering a hypothetical situation in which an endoscopic procedure is being done at an outflow rate of 100 ml/minute, an inflow rate R1 and the cavity pressure being 80 mm Hg. If the surgeon wants to increase the outflow rate to 322 ml/minute by maintaining the cavity pressure at the same value of 80 mm Hg, the outflow rate is increased to 322 ml/minute and the inflow rate is increased by 222 ml/minute, because 322 ml/min−100 ml/min=222 ml/minute. As already mentioned above, if both inflow and outflow rates are increased or decreased by the same magnitude, the cavity pressure does not change. Thus, the final inflow rate becomes R1+222 ml/minute, where R1 was the initial inflow rate. Thus, in the proposed system the cavity pressure and the outflow rate both can be altered absolutely independent of each other without affecting the value of the other parameter.

Mechanical Version of the System

The mechanical version of the system shown in FIG. 4 can be used practically in endoscopic surgeries but it requires a human operator. Thus, the controller based version of the system shall be discussed in subsequent paragraphs.

Controller Based Version of the System

Referring to FIG. 3, this figure shows a schematic diagram of the system with a controller. FIG. 3 and FIG. 4 are similar except that in FIG. 4 the controller system is not included. A tachometer, not shown in the drawings, is coupled to each peristaltic pump and sends information regarding the pump rotation speed to the controller 19 via wires 20 and 23. The pump flow rates being proportional to the pump rotation speed the tachometer signal always conveys flow rate related information to the controller. As already mentioned, both peristaltic pumps have been considered to be similar in all respects because this makes it easier to understand and operate the system. However, the two peristaltic pumps may also be different in context with the inner diameter of the peristaltic pump tubes 4 and 13 but in such case suitable modifications have to be made in the controller programming in order to operate the system as described in this manuscript. The controller also regulates the rotation speed of the two pumps via electrical signals sent through wires 24 and 21. The pressure transducer 17 conveys the pressure signal to the controller via wires 22. On the basis of a pressure feed back signal received from the pressure transducer 17 the controller regulates the rotational speed of the inflow pump 5. The outflow pump 14 works at fixed outflow rates and the flow rate of this pump is also regulated by the controller via suitable electrical signals sent via wires 21. A provision exists by which desired values for P and R2 can be fed into the controller and the values R1, R2 and P can be continuously displayed via suitable display means incorporated in the controller. The controller can be programmed to perform many special functions related to endoscopic surgery which shall be discussed in the following paragraphs.

Method of Operating the Controller Based Version of the System

Referring to FIG. 3, in context with the system at the start of surgery, the surgeon initially selects suitable values for cavity pressure P and outflow rate R2. The desired values of P and R2 are fed into the controller via suitable input means incorporated in the controller. The diameter D at the constriction site 8 remains fixed at some pre selected value. The diameter of the constriction site 8 is so chosen that it suits the operational needs of the endoscopic procedure. The method of selecting a suitable diameter D for the constriction site 8 has already been discussed under the heading "Selection of a suitable diameter for the constriction site." When the system shown in FIG. 3 is operated, the controller 19 instructs the outflow pump 14 via wires 21 to continuously extract fluid out of the body cavity 18 at a desired fixed outflow rate R2. Thus, all through the surgery, the outflow rate remains fixed at R2 irrespective of any internal or external factors unless intentionally changed by the surgeon.

The cavity pressure is sensed by the pressure transducer 17 and a corresponding pressure feedback signal is sent to the controller via wires 22 on the basis of which the controller regulates the inflow rate R1, via wires 24. After the system is made operational, the controller 19 gradually increases the inflow rate up to the point where the desired preset cavity pressure P is achieved. Let the value of the inflow rate at which the desired cavity pressure is achieved be termed as 'R1.final'. It is obvious that the value 'R1.final' is actually determined by the controller by a pressure feed back mechanism and such determination of the value 'R1.Final' is based on the preset values of R2 and P. The controller is so programmed that, once the value 'R1.final' is achieved and is maintained for a desired minimum time interval, for example 10 seconds, after which the controller releases the inflow pump 4 from its pressure feedback control mechanism and allow the inflow pump 4 to operate on its own at an inflow rate 'R1.final' which was determined by the controller. In this manner, the two peristaltic pumps continue to work at fixed flow rates to maintain a desired stable cavity pressure.

The controller is also programmed that in case the cavity pressure subsequently alters, for example due to intravasation, by a desired minimum preset magnitude and for a desired minimum time, which may hypothetically be 10 seconds, the inflow pump 4 again comes under the pressure feedback control of the controller and a new value of 'R1.final' is determined by the controller after which the inflow pump 4 is again allowed to be operated without the pressure feedback mechanism at the newly determined 'R1.final' inflow rate. Such sequences of events continue to occur throughout the endoscopic procedure. Taking an imaginary example, if the total surgical time is 60 minutes, then it may be hypothetically possible to operate the inflow pump independent of the pressure feedback mechanism for 55 minutes and under the control of the pressure feedback mechanism for 5 minutes. However, operating the inflow pump 4 under a pressure feedback mechanism all through the endoscopic procedure can also be incorporated.

The Advantage of Operating the Inflow Pump Independent of the Pressure Feedback Mechanism One reason for operating the inflow pump 4 independent of the pressure feedback mechanism is to avoid unnecessary corrections of minor pressure variations caused by physiological cavity wall contractions. In the present system, the physiological variations in cavity pressure are automatically corrected by the constriction site 8 without the need of a controller. If the cavity contracts a minute quantity of fluid which is pushed out of the cavity escapes via the constriction site 8 towards point 3. The part of tube 7 between point 8 and 3 is at atmospheric pressure, thus the fluid which is expelled from the cavity as a result of a physiological contraction escapes through the constriction site 8 against a zero pressure head, which is—atmospheric pressure. Thus, the transient, insignificant and instantaneous rise and fall in cavity pressure gets stabilized at the desired preset value within a fraction of seconds.

Alternatively, if the cavity expands a suitable volume of fluid is sucked into the cavity from the irrigation circuit, such as from the region of point 6, and this is accompanied by a corresponding transient decrease in the flow rate at which fluid is escaping via the constriction site 8 in the direction of point 3 but if the magnitude of the said physiological expansion is more fluid may even be sucked into the cavity via the constriction site 8. This implies that the constriction site 8 is helping in maintaining a stable cavity pressure despite physiological cavity wall contractions by suitably varying the magnitude of an imaginary fluid flow vector passing through the constriction site 8. Normally, the direction of such imaginary vector is always towards point 6 while its magnitude constantly varies to take care of the pressure changes resulting due to physiological cavity contractions. Normally, a cavity continuously contracts and dilates by approximately the same magnitudes thus there is no logic to check the minor pressure variations emanating from the said contractions. Also, the opening of the constriction site 8 does not allow the said physiological cavity pressure fluctuations to cause any significant cavity wall movement excursions by allowing to and fro movement of flow through its lumen. However, if the pressure changes are made to be corrected by a controller, as is done in the prior art systems, the cavity wall may exhibit significant irregular pressure fluctuations which may result in significant movement excursions of the cavity wall, thus disallowing a predictably stable mechanical stabilization of the cavity walls. However, in the eventuality of fluid intravasation the fall in cavity pressure drop is relatively more permanent in nature thus needs to be corrected by the controller.

As already explained, the controller is so programmed that the inflow pump 4 automatically comes under the pressure feedback control mechanism of the controller in case the cavity pressure alters by a desired minimum preset magnitude and for a desired preset time interval, thus a new 'R1.final' inflow rate is established at which the inflow pump is again allowed to operate without the feedback control of the controller. As a safety precaution, a provision can be made in the controller via suitable input means to fix an upper safe limit for the inflow rate R1 and the cavity pressure P such that these safe limits are not exceeded accidentally.

Controller Programming for Determining the Instantaneous Rate of Fluid Intravasation During Surgery In the above paragraphs, a mechanical method of determining the instantaneous real time instantaneous rate of fluid intravasation without using the controller has been described. However, such mechanical evaluation is subject to human error and is also difficult to repeat multiple times during an endoscopic procedure. Hence, the need arises to continuously determine and display the real time rate of fluid intravasation by the help of the controller. Excess fluid intravasation during an endoscopic procedure can even lead to the patient's death thus it is extremely important for the surgeon to reliably, accurately and constantly know the real time rate of fluid intravasation R3 throughout the endoscopic procedure. In order to determine the real time rate of intravasation, an equation $KP=(R1-(R2+R3))^2$ has been derived where K=constant, P=cavity pressure, R1=inflow rate, R2=outflow rate and R3=instantaneous rate of fluid intravasation. In the equation, the values of P, R1 and R2 are always known by the controller and the value of the constant K can be determined by suitable analytical means. Thus, in the equation, R3 is the only unknown value which can be determined by feeding the expression contained in the said equation into the controller via suitable programming means and directing the controller to continuously determine and display R3.

The controller can be further programmed to carry out multiple other functions related to intravasation such as an alarm being sounded if intravasation of a specific minimum magnitude occurs or if the rate of intravasation rate increases by a specific magnitude. The controller can also be programmed to completely shut down the system in case the rate of intravasation exceeds a specified dangerously high rate.

Selection of a Suitable Diameter for the Constriction Site

If the diameter of the constriction site 8 is very small, then the transient pressure fluctuation in the cavity pressure would be of a relatively larger magnitude and would last for a relatively longer time interval but the associated resultant movement excursion of the cavity wall would be of a relatively small amplitude. Similarly, if the diameter of the constriction site 8 is very large, then the transient cavity pressure fluctuations would be of a relatively smaller magnitude and would last for a relatively shorter time interval but the associated resultant movement excursion of the cavity walls would be of much larger amplitude. These statements are explained by the help of three hypothetical numerical assumptions as stated in Table 1 which is as follows:

movement excursion is relatively more than the nuisance value of the said transient pressure surge. However, the amplitude of the pressure surge should also be not very high because it may promote intravasation and other problems.

Thus, while selecting the diameter of the constriction site two things are kept in mind, the operational needs of the endoscopic procedure as already explained in this paragraph and the anticipated cavity wall contraction and expansion movements. Thus, in those endoscopic procedures where mechanical stability of the cavity walls is important the numerical value of the constriction site diameter D should be relatively smaller.

Referring to FIGS. 3 to 7, the inflow tube 10 and the outflow tube 12 have been shown connected to the inlet and the outlet openings of a cavity 18; however such description is proposed only for the sake of an easier understanding of the system. In practice, the distal end of the inflow tube 10 is connected to an inflow port of a "continuous flow endoscope" and the proximal end of the outflow tube is connected to outflow port of the "continuous flow endoscope."

In the subsequent paragraphs, the advantages and method of attaching and using the endoscope 27 with the described fluid management system shall be discussed.

The Advantages and the Method of Attaching the Endoscope with the Fluid Management System FIG. 1 shows the main block diagram of the invention. FIG. 1 is similar to FIG. 3, except that the tissue cavity 18 has been substituted by the endoscope 27. Though tissue cavity 18 has not been included in FIG. 1, it is deemed to be understood that the distal end of the endoscope 27 has been inserted via a single natural or a single created opening in the said tissue cavity. The distal open end of the inflow tube 10 has been shown connected to the inflow port 33 of the endoscope 27. The proximal open end of the outflow tube 12 has been connected to the outflow port 34 of the endoscope 27.

The fluid management system as described in FIGS. 3, 4, 6 and 7 removes fluid from the tissue cavity 18 by a process of active extraction and not by passive expulsion and such arrangement prevents the cavity 18 from collapsing despite the relatively large lumen diameter of the outflow port 42.

The arrangement shown in FIG. 1 provides a system of distending a body tissue cavity by continuous flow irrigation such that the detached tissue pieces and waste fluid present

TABLE 1

| Serial number of the assumption | A hypothetically assumed numerical value of the constriction site diameter | A hypothetically assumed numerical value of the magnitude of a transient pressure surge associated with a physiological cavity wall contraction movement | A hypothetically assumed time interval for which the said pressure surge exists | A hypothetically assumed magnitude of the associated resultant cavity wall movement excursion |
|---|---|---|---|---|
| 1 | 0.1 mm | 20 mmHg | 3 seconds | 0.5 mm |
| 2 | 1 mm | 5 mmHg | 1 second | 1 mm |
| 3 | 1.5 mm | 1 mmHg | 0.5 seconds | 5 mmHg |

(*Note: A similar table can be hypothetically constructed taking into consideration cavity wall expansion, instead of contraction.)

In context of routine endoscopic procedures, the above mentioned hypothetical situation associated with serial number 2 is most acceptable out of the three hypothetical examples because a high magnitude cavity wall movement excursion is not at all desirable while a moderately high transient pressure surge may be acceptable in most endoscopic procedures. Thus, the nuisance value of a cavity wall inside the cavity 18 is continuously evacuated via the outflow port 34 without the need of withdrawing the endoscope or a part of the endoscope, such as the endoscopic instrument, from the tissue cavity. The evacuated tissue pieces and the waste fluid is finally transported to the waste fluid collecting container 16 via the outflow tube 12 and the waste fluid carrying tube 45. Such an arrangement as shown in FIG. 1 also provides other benefits such as maintaining constant clear endoscopic visualization of the interior of the cavity, maintaining a constant cavity pressure and maintaining a constant mechanical distention of the cavity. The most important, especially in context with the invented system, is that the tissue cavity does not collapse despite a relatively large lumen diameter of the inner sheath 31 and the outflow port 34. Besides these benefits, the arrangement of FIG. 1 provides multiple other benefits such as determining the real time rate of fluid intravasation. In FIG. 1, in case the outflow pump 14 is removed and the distal end of the outflow tube 12 is made to open directly in atmosphere, the cavity would tend to collapse intermittently during an endoscopic procedure, and such an arrangement as seen in the prior art systems has been described in the previous paragraph as "passive expulsion."

Referring to FIG. 1, a remote possibility could be proposed wherein the detached tissue pieces block the lumen 43 of the inner sheath 31 or the outflow port 34. In case of the remote possibility the outflow pump 14, or preferably both pumps 14, 5 could be made to rotate simultaneously in an opposite direction, that is in a direction opposite to the direction of the curved arrows, at a relatively high flow rate and for a relatively short period of time and such action is being termed as "flushing maneuver." The "flushing maneuver" would immediately flush the blocking tissue back into the tissue cavity and normal surgery could continue after this. The "flushing maneuver" could be initiated manually by the surgeon for example by a foot switch. The "flushing maneuver" could also be initiated by the help of a "pressure feedback mechanism" which would require an appropriate programming of the controller. The "pressure feedback mechanism" could utilize the optional outflow pressure transducer 26, or both the pressure transducers 26 and 17.

The endoscope 27 has been included in FIG. 1 but it is also deemed to be included in FIGS. 3, 4, 6 and 7 as well.

Referring to FIG. 1, the endoscope 27 and the fluid management system work in a synergistic manner such that both enhance the efficiency of each other.

The invention is useful since it enhances the patient safety and surgical efficiency in continuous flow irrigation based endoscopic procedures.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A continuous flow irrigation endoscope, comprising:
 a body having a proximal end and a distal end; an outer tube, wherein at least a portion of the outer tube has a first diameter; an inner tube located within the outer tube, the inner tube having a second diameter which is smaller than the first diameter, wherein the inner tube further defines within the outer tube a closed cavity within the body of the endoscope, the closed cavity surrounding an entire circumference of the inner tube; and wherein the endoscope further comprises:
 an inflow port formed on an outer circumferential portion of the outer tube at a proximal end thereof and being configured to allow fluid to enter through the outer tube and into the closed cavity;
 a plurality of perforations formed on an outer circumferential portion of the outer tube at a distal end thereof and being configured to allow fluid to exit the closed cavity;
 an outflow port formed on an outer circumferential portion of the inner tube at a proximal end thereof and being configured to allow fluid and/or tissue debris to exit the body of the endoscope through the inner tube;
 wherein a cross-sectional area of the outflow port is equal to a cross-sectional area of the inner tube,
 wherein a cross-sectional area of the outflow port is equal to a cross-sectional area of a distally located opening being in communication with the outflow port, and wherein the inner and the outer tubes touch each other at their distal most ends, the distally located opening representing openings of both the tubes at a position where the tubes make a fluid tight contact with each other, and
 wherein the inner channel accommodates an optical channel.

2. The endoscope of claim 1, wherein a cross-sectional area of the outflow port is at least equal to a cross-sectional area of the inner tube.

3. The endoscope of claim 1, wherein the inner tube is a surgical channel for an instrument selected from the group consisting of an electrosurgical cutting loop, electrode, electrosurgical instrument, roller ball electrode and right angle electrode.

4. The endoscope of claim 1, wherein the plurality of perforations allow irrigation fluid to enter a tissue cavity undergoing a surgical procedure.

5. The endoscope of claim 1, wherein the outflow port has an elliptical or round cross-section.

6. The endoscope of claim 1, wherein the outflow port has an elliptical cross-section.

7. The endoscope of claim 1, wherein the inflow port is in communication with an inflow pump and wherein the outflow port is in communication with an outflow pump.

8. A continuous flow irrigation system, comprising:
 a resectoscope-based endoscope comprising: the endoscope comprising a body having a proximal end and a distal end; an outer tube, wherein at least a portion of the outer tube has a first diameter; an inner tube located within the outer tube, the inner tube having a second diameter which is smaller than the first diameter, wherein the inner tube further defines within the outer tube a closed cavity within the body of the endoscope, the closed cavity surrounding an entire circumference of the inner tube; and wherein the endoscope further comprises:
 an inflow port formed on an outer circumferential portion of the outer tube at a proximal end thereof and being configured to allow fluid to enter through the outer tube and into the closed cavity;
 a plurality of perforations formed on an outer circumferential portion of the outer tube at a distal end thereof and being configured to allow fluid to exit the closed cavity;
 an outflow port formed on an outer circumferential portion of the inner tube at a proximal end thereof and being configured to allow fluid and/or tissue debris to exit the body of the endoscope through the inner tube;
 wherein a cross-sectional area of the outflow port is equal to a cross-sectional area of the inner tube,
 wherein a cross-sectional area of the outflow port is equal to a cross-sectional area of a distally located opening being in communication with the outflow port, and wherein the inner and the outer tubes touch each other at their distal most ends, the distally located opening representing openings of both the tubes at a position where the tubes make a fluid tight contact with each other, an inflow pump connected to the inflow port of the resectoscope-based endoscope; and an outflow pump connected to the outflow port of the resectoscope-based endoscope.

9. The system of claim 8, wherein at least one of the inflow pump and the outflow pump is a peristaltic pump, piston pump, gear pump or diaphragm pump.

10. The system of claim 8, wherein the inflow pump is connected to a fluid source reservoir, and wherein the system further comprises a tube having a variable size constriction site provided between the fluid source reservoir and the inflow port of the resectoscope-based endoscope, the tube providing a route for any excess fluid being pumped by the inflow pump to bypass the inflow pump.

11. The system of claim 8, wherein the resectoscope-based endoscope further comprises an optical channel located inside the inner lumen, the optical channel being about parallel to the longitudinal axis of the outer and inner sheaths.

12. A continuous flow irrigation system for an endoscopic procedure, the system comprising:

an endoscope comprising: the endoscope comprising a body having a proximal end and a distal end; an outer lumen, wherein at least a portion of the outer lumen has a first diameter; an inner lumen located within the outer lumen, the inner lumen having a second diameter which is smaller than the first diameter, wherein the inner lumen further defines, within the outer lumen, a closed cavity within the body of the endoscope, the closed cavity surrounding an entire circumference of the inner lumen; and wherein the endoscope further comprises:

an inflow port formed on an outer circumferential portion of the outer lumen at a proximal end thereof and being configured to allow fluid to enter through the outer lumen and into the closed cavity;

a plurality of perforations formed on an outer circumferential portion of the outer lumen at a distal end thereof and being configured to allow fluid to exit the closed cavity;

an outflow port formed on an outer circumferential portion of the inner lumen at a proximal end thereof and being configured to allow fluid and/or tissue debris to exit the body of the endoscope through the inner lumen;

wherein a cross-sectional area of the outflow port is equal to a cross-sectional area of the inner lumen, wherein a cross-sectional area of the outflow port is equal to a cross-sectional area of a distally located opening being in communication with the outflow port, and wherein the inner and the outer lumens touch each other at their distal most ends, the distally located opening representing openings of both the lumens at a position where the lumens make a fluid tight contact with each other, and wherein the inner channel accommodates an optical channel a first peristaltic pump connecting a fluid source reservoir to the inflow port of the endoscope via an inflow tube;

a second peristaltic pump connecting a waste fluid reservoir to the outflow port of the endoscope; and a tube having a controllable constriction site provided between the fluid source reservoir and the inflow port of the endoscope, the tube providing a route for any excess fluid being pumped by the first peristaltic pump to bypass the first peristaltic pump.

13. The system of claim 12, wherein the inner lumen of the endoscope is configured to allow passage of a surgical instrument to effectuate at least a surgical procedure on tissue of a body cavity.

14. The system of claim 13, wherein the surgical procedure is selected from the group consisting of hysteroscopic endometrial resection, hysteroscopic fibroid resection, hysteroscopic polyp resection, hysteroscopic septoplasty, hysteroscopic adhesiolysis, hysteroscopic endometrial ablation, trans uretheral resection of the prostate, transuretheral resection of bladder tumors and arthroscopy.

* * * * *